United States Patent [19]
Das et al.

[11] Patent Number: 5,948,396
[45] Date of Patent: Sep. 7, 1999

[54] HAIR FIXATIVE AMPHOTERIC POLYMER COMPOSITION

[75] Inventors: Suryya K. Das, Pittsburgh; Soner Kilic, Gibsonia; William C. Allison, Murrysville, all of Pa.

[73] Assignee: PPG Industries Ohio, Inc., Cleveland, Ohio

[21] Appl. No.: 08/921,483

[22] Filed: Sep. 2, 1997

Related U.S. Application Data

[63] Continuation of application No. 08/650,935, May 17, 1996, abandoned, which is a continuation of application No. 08/263,103, Jun. 21, 1994, abandoned.

[51] Int. Cl.$^6$ ............................... A61K 7/00; A61K 7/06
[52] U.S. Cl. ..................... 424/70.17; 424/70.15; 424/70.16; 424/70.17; 424/DIG. 2; 424/70.11
[58] Field of Search ............... 424/70.11, 70.15, 424/70.16, 70.17, DIG. 2

[56] References Cited

U.S. PATENT DOCUMENTS

| | | | |
|---|---|---|---|
| 3,726,288 | 4/1973 | Nowak et al. | 424/47 |
| 3,927,199 | 12/1975 | Micchelli et al. | 424/78.03 |
| 3,958,581 | 5/1976 | Abigg | 424/47 |
| 3,981,987 | 9/1976 | Linke | 424/47 |
| 4,165,367 | 8/1979 | Chakrabarti | 424/47 |
| 4,192,861 | 3/1980 | Micchelli et al. | 424/47 |
| 4,196,190 | 4/1980 | Gehman et al. | 424/47 |
| 4,933,170 | 6/1990 | Nowak | 424/47 |
| 5,068,099 | 11/1991 | Sramek | 424/47 |
| 5,126,124 | 6/1992 | Tazi et al. | 424/47 |
| 5,160,729 | 11/1992 | Login et al. | 424/47 |
| 5,304,368 | 4/1994 | Shernov et al. | 424/47 |

*Primary Examiner*—Sally Gardner-Lane
*Attorney, Agent, or Firm*—Kenneth J. Stachel; Dennis G. Millman

[57] ABSTRACT

An amphoteric, hair fixative polymer for use in hair sprays, gels, and the like contains 40–90 percent of a hydroxyl-containing ethylenically unsaturated monomer, 1–20 percent of an acid-containing ethylenically unsaturated monomer, and 1–20 percent of an amine-containing ethylenically unsaturated monomer. The polymer has hydroxyl, acid and amine functionalities and, while being insoluble in water, can be solubilized in water by the use of amine neutralizers, acidic neutralizers, or by solubilizing in alcohol-water mixtures. The polymers provide hair fixatives that are fast drying, and have excellent curl retention with low curl droop.

21 Claims, No Drawings

HAIR FIXATIVE AMPHOTERIC POLYMER COMPOSITION

This application is a continuation of application Ser. No. 08/650,935, filed May 17, 1996, now abondoned which is a continuation of application Ser. No. 08/263,103, filed Jun. 21, 1994 now abandoned.

FIELD OF THE INVENTION

The present invention relates to hair fixative polymer compositions that can be used in hair fixative formulations and which provide fast drying, excellent curl retention with low curl droop, and a soft, silky feel to the touch.

BACKGROUND OF THE INVENTION

Hair fixative formulations, containing hair fixative polymers, have been extensively used in aerosol sprays, pump sprays, mousses and gels. Typically these hair fixative formulations make use of large amounts of alcohol, most often ethanol, in amounts of 80% or more by weight, as the principle solvent. These alcohol solvents are designated as volatile compounds and contribute in large part to the volatile content, (VOC), of these formulations. Efforts to reduce the VOC, and thereby reduce the alcohol content, of hair fixative formulations has usually involved the replacement of some or all of the alcohol with water. Hair fixative polymers which are dissolved in alcohol-water mixtures, or water alone, typically require the addition of a volatile amine neutralizing agent. The amine neutralizing agent forms a salt with pendant acid groups on the polymer, allowing the polymer to be solubilized into the water or alcohol-water mixture. Upon application, the amine, and alcohol if present, is volatilized and the hair fixative polymer becomes less soluble in the remaining water droplets and sticks to the hair shafts. Unfortunately, the majority of volatile amine neutralizing agents are also considered to be toxic, to some degree. Thus it would be desirable to develop hair fixative polymers which can be solubilized in water or in water-alcohol mixtures without reliance on the use of amine neutralizers.

In addition to providing hair fixatives having reduced VOC contents, it is important that the polymers used provide properties which enhance the hair fixative formulations. For example, the polymer should have fast drying properties such that upon application to the hair, excessive drying time is not required. Also, while fast drying is important, it is also important that the hair fixative polymer also provide for low curl droop upon application and high curl retention under high humidity conditions. The polymer compositions used in hair fixative formulations should thus provide a number of beneficial physical properties on use while the same should be solubilized in a manner which would enable reduction of VOC content in hair fixative formulations using such polymers. Furthermore, it should provide manageability of the hair upon application and drying, and it should be easily removable upon shampooing.

SUMMARY OF THE INVENTION

A hair fixative polymer composition is provided which comprises an amphoteric polymer that is water insoluble but which can be solubilized in water by either adding an acid neutralizing agent, or adding an amine neutralizing agent, or adding a low-boiling, water miscible alcohol to water to solubilize or disperse the polymer therein.

The hair fixative polymer is an amphoteric polymer that contains, by weight, ethylenically unsaturated monomers that comprise 40–90 percent of a hydroxyl-containing ethylenically unsaturated monomer which provides hydroxyl functionality to the polymer; 1–20 percent of an acid-containing ethylenically unsaturated monomer which provides carboxy functionality to the polymer; and 1–20 percent of an amine-containing ethylenically unsaturated monomer which provides amine functionality to the polymer. The amphoteric polymer may also contain up to 40 percent of ethylenically unsaturated monomers that are devoid of acid, amine, and hydroxyl functionalities. For any particular amphoteric polymer, the total of the weight percentages of the monomers equals 100.

A preferred amphoteric polymer of the present invention contains by weight, 40–90 percent of 2-hydroxyethyl methacrylate, 1–20 percent by weight of acrylic acid or methacrylic acid, 1–20 percent of N,N-dimethylaminoethyl methacrylate, and 10–30 percent of styrene or methyl methacrylate.

The hair fixative amphoteric polymers of the present invention may be used in hair fixative compositions such as sprays, gels, and the like for hair fixing purposes.

DETAILED DESCRIPTION

The present invention provides an amphoteric polymer, usable as a hair fixative polymer composition, that is water insoluble but which can be either 1) solubilized or dispersed in water as a salt of a water soluble acid (cationic form), 2) solubilized or dispersed in water as a salt of a water soluble amine (anionic form), or 3) solubilized or dispersed in an alcohol-water mixture (nonionic form). The polymer contains hydroxy, acid and amine functionalities in a proportion sufficient to render the same insoluble in water but solubilizable by volatile acids or amines.

The hair fixative polymer composition contains 40–90 percent by weight, and preferably 50 to 75 percent, of a hydroxyl-containing ethylenically unsaturated monomer which provides hydroxyl functionality to the resultant polymer. Typically useful hydroxyl-containing ethylenically unsaturated monomers are hydroxy alkyl acrylates and hydroxy alkyl methacrylates such as hydroxyethyl acrylate, hydroxyethyl methacrylate, hydroxypropyl acrylate, hydroxypropyl methacrylate, hydroxybutyl acrylate and hydroxybutyl methacrylate, and the like.

The hair fixative polymer composition also contains 1–20 percent by weight, and preferably 2 to 15 percent, of an acid-containing ethylenically unsaturated monomer. The term "acid-containing ethylenically unsaturated monomer" as used herein describes a monomer that will provide pendant acid groups in polymer and thus provides acid functionality to the resultant polymer. Particularly useful acid-containing ethylenically unsaturated monomers include acrylic acid and methacrylic acid, while other such acid-containing ethylenically unsaturated monomers usable include, 10-undecenoic acid, crotonic acid, beta-carboxyethyl acrylate, and the like.

A third component of the hair fixative polymer composition is an amine-containing ethylenically unsaturated monomer, which provides pendant amine groups to the polymer, and is present in an amount of 1–20 percent by weight, and preferably about 5 to 15 percent. Such amine-containing monomers include amine functional acrylates and methacrylates, such as N,N-dimethylaminoethyl methacrylate, tert-butylaminoethyl methacrylate, N,N-diethylaminoethyl methacrylate, and the like.

Optionally, about 0–40 percent by weight, and preferably about 10 to 20 percent, of an ethylenically unsaturated monomer that is devoid of acid, amine and hydroxyl functionalities may be added to the polymer composition. Such a monomer may be an alkyl ester of acrylic or methacrylic acid, such as methyl methacrylate, ethyl methacrylate, butyl methacrylate, ethyl acrylate, butyl acrylate, 2-ethylhexyl acrylate, vinyl aromatic monomers such as styrene and vinyl toluenei nitrile monomers such as acrylonitrile and methacrylonitrile; vinyl esters such as vinyl acetate; and vinyl amides such as acrylamide and N-alkylacrylamides and cyclic amides.

An especially useful amphoteric polymer is one containing about 40–90 percent by weight of 2-hydroxyethyl methacrylate: 1–20 percent by weight of acrylic acid: 1–20 percent by weight of N,N-dimethylaminoethyl methacrylate; and about 10–30 percent by weight of styrene or methyl methacrylate.

The polymers of the present invention may be prepared by conventional solution polymerization techniques which are well known in the art. This polymerization is usually carried out in an organic solvent under reflux conditions with an appropriate initiator having a specific half-life of decomposition. The polymer conversion is usually better than 95 percent. The free monomers after polymerization can be reduced by further addition of initiator and longer hold time or both, as necessary. It can be further reduced if necessary by redox initiators in the aqueous medium after inversion from non-aqueous medium in cases where such inversion is possible and acceptable.

Alternately, the polymer may be prepared by aqueous emulsion or dispersion polymerization, where the polymerization is carried out in the medium of water, in the presence of surface active agents, by water soluble initiators which are primarily inorganic peroxydisulfates.

The amphoteric polymer of the present invention should have a molecular weight (number average molecular weight) of between about 1500 to 1,000,000, preferably between about 2500 to 100,000, and most preferably between about 5000 to 25,000, and a calculated glass transition temperature (Tg) of between 40–80° C.

The amphoteric polymers of the present invention are insoluble in water but, due to the acid functionality and the amine functionality present, the amphoteric polymer can be solubilized or dispersed in water either anionically as a salt of a water soluble amine, or cationically as a salt of a water soluble acid, or nonionically by dissolution in an alcohol-water mixture where the ratio of the alcohol and water depends upon the particular polymer composition. The amines or acids used to solubilize the polymer are preferably volatile compounds such that upon their release during drying the polymer becomes insoluble in water.

Amines that are usable as neutralizing agents include 2-dimethylaminoethanol N,N-dimethylethanolamine), 2-amino-2-methyl-1-propanol, 3-dimethylamino-1-propanol, 3-dimethylamino-2-propanol, 1-amino-2-propanol, ethanolamine, ammonia, and the like.

Acids that are usable as neutralizing agents include carbonic, formic, acetic, lactic, trifluoro acetic acid, and the like, with carbonic and acetic acids being preferred.

The amount of amine or acid added to the amphoteric polymer is that sufficient to solubilize the polymer in water or a predetermined alcohol-water mixture. Between about 1–100 percent of the carboxyl or amine pendant groups should be neutralized, with about 20 to 50 percent of total neutralization preferred.

Or, the amphoteric polymer may be dissolved in a mixture of a low-boiling, water miscible alcohol and water, the alcohols being selected from a monohydric alcohol having 2 or 3 carbon atoms, such as ethanol or propanol. The amount of alcohol added to dissolve the amphoteric polymer, in nonionic polymer mode, will depend on the particular polymer and is an amount sufficient to disperse or solubilize the polymer. The percent of water in the total solution will be between 0 to 85 percent, preferably between about 30 to 80 percent, and most preferably between about 70 to 80 percent.

In the formation of hair fixative formulations incorporating the present hair fixative polymers, propellants, known in the art, would be added to polymer solutions for use in hair sprays. An especially useful propellant would be carbon dioxide which can also be present as a neutralizing agent for cationic solubilization of the hair fixative polymer. The propellant is added in an amount sufficient to enable application of a solution of the hair fixative polymer, in a desired amount, to hair, as is known in the art.

The following examples further illustrate the present invention in its preferred embodiments.

As used in the body of the present specification, examples, and claims, all percents, ratios and parts are by weight unless otherwise specifically indicated.

In the following examples, the Tg's, (glass transition temperatures), were determined through use of the Fox equation, the % weight solids were determined at a temperature of 110° C. for one hour and the number average molecular weights were determined from gel permeation chromatography using polystyrene as the standard and N,N-dimethylformamide as the solvent.

The following examples, 1 through 5, describe the preparation of polymers which are particularly useful in the practice of the invention.

EXAMPLE 1

This example illustrates the preparation of an amphoteric acrylic polymer utilized in a hair fixative composition according to the present invention.

The following were charged to a suitable reaction vessel equipped with an agitator, a reflux column, a thermocouple and a heating mantle:

| Material | Weight (grams) |
|---|---|
| Charge-1 | |
| Ethanol | 935.0 |
| Charge-2 | |
| VAZO-67[(1)] | 38.2 |
| Acrylic acid | 18.0 |
| 2-Hydroxyethyl methacrylate | 513.3 |
| N,N-Dimethylaminoethyl methacrylate | 79.2 |
| Methyl methacrylate | 152.6 |
| Ethanol | 300.0 |

[(1)]Vazo-67 chemically is 2,2'-Azobis-(2-methylbutyronitrile) and is available commercially from E. I. duPont de Nemours and Company.

(1) Vazo-67 chemically is 2,2'-Azobis-(2-methylbutyronitrile) and is available commercially from E. I. duPont de Nemours and Company.

Charge-1 was initially added to the reaction vessel and heat was applied with agitation until a temperature of reflux was reached. Charge-2 was then fed into the reaction vessel in a continuous manner over a period of three hours. The reflux temperature was maintained throughout the addition of the Charge 2. With the completion of the addition of Charge 2, the reaction mixture was held for an additional three hours at the reflux temperature. The contents of the reaction vessel were then cooled and transferred to a suitable container. The resultant polymer solution had a total solids content, based on total solution weight, of 42.5%, a number average molecular weight of 9306, and a Tg (glass transition temperature) of 60.5° C.

EXAMPLE 2

This example illustrates the preparation, in accordance with the method described in Example 1, of an amphoteric styrene-containing acrylic polymer utilized in a hair fixative composition according to the present invention.

The following were charged to a suitable reaction vessel equipped with an agitator, a reflux column, a thermocouple and a heating mantle:

| Material | Weight (grams) |
|---|---|
| Charge-1 | |
| Ethanol | 467.5 |
| Charge-2 | |
| Vazo-67 | 19.1 |
| Acrylic acid | 9.0 |
| 2-Hydroxyethyl methacrylate | 256.7 |
| N,N-Dimethylaminoethyl methacrylate | 39.6 |
| Styrene | 76.3 |
| Ethanol | 150.0 |

The resultant polymer solution had a total solids content, based on total solution weight, of 40.5%, a number average molecular weight of 9596, and a Tg of 59.70° C.

EXAMPLE 3

This example illustrates the preparation, in accordance with the method described in Example 1, of an amphoteric acrylic polymer with a lower Tg than those of Examples 1 and 2, which can be utilized in a hair fixative composition according to the present invention.

The following were charged to a suitable reaction vessel equipped with an agitator, a reflux column, a thermocouple and a heating mantle:

| Material | Weight (grams) |
|---|---|
| Charge-1 | |
| Ethanol | 467.5 |
| Charge-2 | |
| Vazo-67 | 19.1 |
| Acrylic acid | 9.0 |
| 2-Hydroxyethyl methacrylate | 294.8 |
| N,N-Dimethylaminoethyl methacrylate | 39.6 |
| Methyl methacrylate | 38.2 |
| Ethanol | 150.0 |

The resultant polymer solution had a total solids content, based on total solution weight, of 40.6%, a number average molecular weight of 10,560, and a Tg of 56.0° C.

EXAMPLE 4

This example illustrates the preparation of a cationic amphoteric acrylic polymer, in an isopropanol and water solvent mixture, with the isopropanol distilled off after neutralization with acetic acid, which can be utilized in a hair fixative composition according to the present invention.

The following were charged to a suitable reaction vessel equipped with an agitator, a reflux column, a thermocouple and a heating mantle:

| Material | Weight (grams) |
|---|---|
| Charge-1 | |
| Isopropanol | 300.0 |
| Deionized water | 167.5 |
| Charge-2 | |
| Vazo-67 | 19.0 |
| Acrylic acid | 9.0 |
| 2-Hydroxyethyl methacrylate | 331.2 |
| N,N-Dimethylaminoethyl methacrylate | 39.6 |
| Isopropanol | 150.0 |
| Charge-3 | |
| Glacial acetic acid | 3.8 |
| Charge-4 | |
| Deionized water | 1000.0 |

Charge-1 was initially added to the reaction vessel and heat was applied with agitation until a temperature of reflux was reached. Charge-2 was then fed into the reaction vessel in a continuous manner over a period of three hours. The reflux temperature was maintained throughout the addition of Charge 2. With the completion of the addition of Charge 2, the reaction mixture was held for an additional three hours at the reflux temperature. At this point, the resultant polymer solution was found to have a total solids content, based on total solution weight, of 40.6% and a number average molecular weight of 13,728. The contents of the reaction vessel were then cooled to a temperature of 76° C., after which Charge-3 was added. Charge-4 was then added and the contents of the reaction vessel were heated to a temperature at which an azeotropic distillation of the isopropanol was performed. After the completion of the azeotropic distillation of the isopropanol, the contents of the reaction vessel were cooled and transferred to a suitable container. The resulting aqueous dispersion was found to have a total solids content, based on total solution weight, of 32.0%, a pH of 6.60 and a Tg of 51.70° C.

EXAMPLE 5

This example illustrates the preparation, in accordance with the method described in Example 4, of an anionic amphoteric acrylic polymer, in an isopropanol and water solvent mixture with the isopropanol distilled off after neutralization with N,N-dimethylethanol amine, which can be utilized in a hair fixative composition according to the present invention.

The following were charged to a suitable reaction vessel equipped with an agitator, a reflux column, a thermocouple and a heating mantle:

| Material | Weight (grams) |
|---|---|
| Charge-1 | |
| Isopropanol | 300.0 |
| Deionized water | 167.5 |
| Charge-2 | |
| Vazo-67 | 19.0 |
| Acrylic acid | 9.0 |

-continued

| Material | Weight (grams) |
| --- | --- |
| 2-Hydroxyethyl methacrylate | 331.2 |
| N,N-Dimethylaminoethyl methacrylate | 39.6 |
| Isopropanol | 150.0 |
| Charge-3 | |
| N,N-Dimethylethanol amine | 11.1 |
| Charge-4 | |
| Deionized water | 1000.0 |

The resulting anionic aqueous dispersion was found to have a total solids content, based on total solution weight, of 29.3%, a pH of 8.84 and a Tg of 51.7° C.

EXAMPLE 6

Hair fixative polymer compositions of the present invention were tested to evaluate various hair fixative properties, such as Curl Retention, Initial Droop and Drying Time according to the following procedures.

Curl Retention

Curl retention evaluation of the hair fixative polymer compositions of the present invention was made using 5 tresses (virgin European brown hair, 8" long, 2 gm) for each polymer. Each tress was prepared by first washing with a 1% sodium lauryl sulfate solution at 45° C. for 60 seconds. The tresses were then rinsed in running tap water at 40–45° C. for 60 seconds, the rinsed tresses drained for three minutes and combed out to remove excess water and twists. Using a syringe, 1.2 mls of polymer solution (1.5% polymer in ethanol) were applied to each tress and the polymer solution combed through the tress. Each tress was then wrapped onto a ⅝" diameter mandril and dried in an oven at 60° C. for 90 minutes. The tress was then removed from the mandril and mounted in a glovebox at 70–75° F. at 85–90% relative humidity. The initial curl length was then recorded. The curl length was further recorded at regular time intervals through a 2-hour period. The curl retention (% CR) was calculated at each time interval for each tress as follows:

$$\% CR = \frac{(L_t - L_x) \times 100}{(L_t - L_i)}$$

$CR$ = Curl Retention
$L_t$ = Tress Length = 8"
$L_x$ = Curl Length at time $x$
$L_i$ = Curl Length at time 0

The average % Curl Retention for the 5 tresses at each time interval was taken to get a single value. This described method is designated as Method 1.

A second method, Method 2, was also used for some Curl Retention evaluation which was the same procedure as Method 1, except for the following alterations:

a) the 1.2 ml polymer solution was a solution of 1.5% polymer in a 55% ethanol—43.5% water mixture;

b) after wrapping on the ⅝" diameter mandril, the tress was dried overnight at 70–75° F. and 50–60% relative humidity; and c) the curl length was recorded at regular time intervals through a 6-hour period.

Initial Droop

Initial droop evaluation of the hair fixative polymer compositions of the present invention was made using 5 tresses, with comparable tresses used, and shampooing and rinsing the same as described with the Curl Retention method. After the rinsing, the wet tress was then wound around a ⅝" diameter mandril and dried in an oven at 50° C. for 20–23 hours. The tress was slid off the mandril and mounted at ambient conditions. The initial curl length was measured. Using an Emson Z-VOC pump. Series 040, at a distance of 7", 6 pumps of polymer solution (1.56 polymer, 55% ethanol and 43.5% water) were applied onto the tress, and a timer started. The curl length was then measured after 1, 2 and 3 minutes. The % Droop was calculated as follows:

$$\% \text{Droop} = 100 - (\% \text{ Curl Retention})$$
$$= \frac{100 - (L_t - L_x) \times 100}{(L_t - L_i)}$$

$CR$ = Curl Retention
$L_t$ = Tress Length = 8"
$L_x$ = Curl Length at time $x$
$L_i$ = Curl Length at time 0

The average of the % Droop values for the 5 tresses was used to calculate the Average % Droop at 1, 2 and 3 minutes.

Drying Time

Method A (Tactile Endpoint)

A Sag and Levelling Test Chart (The Laneto Co., Ho-Ho-Kus, N.J.), was vertically mounted with the back of the board facing forward. Using an Emson Z-VOC pump, series 040, a solution of polymer (1.5% polymer in 55% ethanol and 43.5% water) was pumped once from a distance of 8" onto the back of the board and a timer started. The board was observed through an oblique angle: a bright reflection could be seen off wet areas. The areas assume a matte appearance as they dry. Once the wet area took on a matte appearance, the area was tapped lightly with a finger, feeling for residual tackiness left by the polymer. Tapping was continued until no tackiness was evident and the area felt the same as a non-sprayed area. This time was recorded as the drying time.

Method B (Visual Endpoint)

A standard 8.5×11" sheet of photocopy paper was vertically mounted. Using an Emson Z-VOC pump, series 040, a solution of polymer (1.5% solution of polymer in 556 ethanol and 43.5% water) was pumped twice from a distance of 7" onto the sheet and a timer started. The sheet was placed on a Logan Desktop Lightbox on which two sheets of polarizing film were set at right angles to each other, making a deep blue light. The wet areas of the paper were clearly visible since they transmitted this light to a much greater extent than did the dry areas. As the paper dried, it became more opaque. The drying time was noted when there were no longer any areas transmitting the cross-polarized light.

The Curl Retention, Initial Droop and Drying Time of various of the polymer compositions produced in Examples 1–5 were evaluated according to the aforementioned procedures and are listed in Table I.

TABLE I (Curl Retention)

| | Curl Retention (%) | |
| --- | --- | --- |
| Polymer | Method 1 | Method 2 |
| Gantrez ® ES-225[1] (Control) | 88.0 | — |
| Polymer of Example 4 | 98.6 | — |
| Polymer of Example 5 | 95.9 | — |
| Water (control) | — | 52.2 |
| Amphomer[2] (control) | — | 90.0 |
| Polymer of Example 1 | — | 96.5 |

TABLE I-continued (Curl Retention)

| Polymer | Curl Retention (%) | |
| --- | --- | --- |
| | Method 1 | Method 2 |
| Polymer of Example 2 | — | 97.9 |
| Polymer of Example 3 | — | 97.9 |

(1)an ethyl half-ester of a linear copolymer of methylvinylether and maleic anhydride having a molecular weight of about 70,000 available from ISP Corporation.
(2)an octylacrylamide/acrylates/butylaminoethyl methacrylate polymer (See U.S. Pat. No. 4,192,861) available from National Starch and Chemical Corporation.

(Initial Droop and Drying Time)

| Polymer | Initial Droop (%) | | | Drying Time (Seconds) | |
| --- | --- | --- | --- | --- | --- |
| | 1 min | 2 min | 3 min | Method A | Method B |
| Gantrez ® ES-225 (control) | 7.5 | 8.8 | 10.4 | 86 | 243 |
| Polymer prepared in accordance with Example 4 | 3.9 | 5.4 | 7.0 | 20 | 68 |

The amphoteric polymers in a cationic state of the present invention have the additional advantage in that additions of an acid to neutralize the same provides a non-toxic neutralizer which is faster evaporating and enhances faster drying, which is an important factor in hair fixatives. Furthermore, the acid neutralization provides a better adhesion to the hair by the acid-amine coordination. This is believed to be because hair is amphoteric and has an isoelectric point at a pH of about four. As a result, at a pH higher than about four, it is in a anionic state and thus adheres well to the cationic polymer, where adhesion by coordination also promotes faster drying. Also, the acid functionalities of the amphoteric polymer not only provide ionic cross-linking insolubilization and faster drying, but such are needed for ease of removal upon shampooing. A polymer without such acid functionality would be difficult to remove.

What is claimed is:

1. A hair fixative amphoteric polymer composition comprising: 40–90 percent by weight of a hydroxyl-containing ethylenically unsaturated monomer which provides hydroxyl functionality to the polymer; 1–10 percent by weight of an acid-containing ethylenically unsaturated monomer which provides carboxy functionality to the polymer; 1–20 percent by weight of an amine-containing ethylenically unsaturated monomer which provides amine functionality to the polymer; and 0 to 30 percent by weight of an ethylenically unsaturated monomer devoid of acid, amine and hydroxyl content, where when this monomer is a vinyl amide the amount of the monomer is up to 20 percent by weight; and wherein the total of the weight percentages for the monomers is 100; and said polymer composition being insoluble in water but solubilizable in water by at least one of the following solubilization steps;

1) addition of a neutralizing agent comprising an acid,
2) addition of a neutralizing agent comprising an amine, and
3) addition of a water miscible alcohol.

2. The hair fixative amphoteric polymer composition as defined in claim 1 wherein said hydroxyl-containing ethylenically unsaturated monomer is 2-hydroxyethyl methacrylate.

3. The hair fixative amphoteric polymer composition as defined in claim 1 wherein said acid-containing ethylenically unsaturated monomer is selected from the group consisting of acrylic acid, methacrylic acid, 10-undecenoic acid, crotonic acid, and beta-carboxyethyl acrylate.

4. The hair fixative amphoteric polymer composition as defined in claim 1 wherein said amine-containing ethylenically unsaturated monomer is N,N-dimethylaminoethyl methacrylate.

5. The hair fixative amphoteric polymer composition as defined in claim 1 wherein said acid neutralizing agent is selected from the group consisting of carbonic, formic, acetic, lactic, and trifluoro acetic acid.

6. The hair fixative amphoteric polymer composition as defined in claim 1 wherein said amine neutralizing agent is selected from the group consisting of ammonia, N,N-dimethylethanolamines 2-amino-2-methyl-1-propanol; 3-dimethylamino-1-propanol; 3-dimethylamino-2-propanol; 1-amino-2-propanol, ethanolamine, and ammonia.

7. The hair fixative amphoteric polymer composition as defined in claim 1 wherein said water miscible alcohol is ethanol.

8. The hair fixative amphoteric polymer composition as defined in claim 1 wherein said polymer composition has a number average molecular weight of between 1,500 and 25,000.

9. The hair fixative amphoteric polymer composition as defined in claim 1 wherein said polymer composition has a glass transition temperature of between 40–80° C.

10. A hair fixative amphoteric polymer composition as defined in claim 1 wherein said hydroxyl-containing ethylenically unsaturated monomer is present in an amount of 50–75 percent, said acid-containing ethylenically unsaturated monomer is present in an amount of 2–10 percent, said amine-containing ethylenically unsaturated monomer is present in an amount of 5–15 percent, and said ethylenically unsaturated monomer devoid of acid, amine and hydroxyl content is present in an amount of 10–20 percent.

11. A hair fixative amphoteric polymer composition as defined in claim 10 wherein said hydroxyl-containing ethylenically unsaturated monomer is 2-hydroxyethyl methacrylate, said acid-containing ethylenically unsaturated monomer is selected from the group consisting of acrylic acid and methacrylic acid, said amine-containing ethylenically unsaturated monomer is N,N-dimethylaminoethyl methacrylate, and said ethylenically unsaturated monomer devoid of acid, amine and hydroxyl content is selected from the group consisting of styrene and methyl methacrylate.

12. A hair fixative amphoteric polymer composition consisting essentially of an amphoteric polymer containing: 40–90 percent by weight of a hydroxyl-containing ethylenically unsaturated monomer which provides hydroxyl functionality to the polymer; 1–20 percent by weight of an acid-containing ethylenically unsaturated monomer which provides carboxy functionality to the polymer; 1–20 percent by weight of an amine-containing ethylenically unsaturated monomer which provides amine functionality to the polymer; and 0 to 40 percent by weight of an ethylenically unsaturated monomer devoid of acid, amine and hydroxyl content; said polymer composition being insoluble in water but solubilizable in water by addition of an acid neutralizing agent.

13. A hair fixative amphoteric polymer composition consisting essentially of an amphoteric polymer containing: 40–90 percent by weight of 2-hydroxyethyl methacrylate which provides hydroxyl functionality to the polymer; 1–10 percent by weight of an acid-containing ethylenically unsaturated monomer selected from the group consisting of acrylic acid and methacrylic acid which provides carboxy functionality to the polymer; 1–20 percent by weight of N,N-dimethylaminoethyl methacrylate which provides amine functionality to the polymer; and 0 to 40 percent by weight of an ethylenically unsaturated monomer devoid of acid, amine and hydroxyl content, selected from the group consisting of styrene and methyl methacrylate; said polymer composition being insoluble in water but solubilizable in water by at least one of the following solubilization steps;

1) addition of a neutralizing agent comprising an acid,
2) addition of a neutralizing agent comprising an amine, and
3) addition of a low-boiling, water miscible alcohol.

14. A hair fixative formulation comprising:
    a) a solution of a hair fixative amphoteric polymer composition comprising 40–90 percent by weight of a hydroxyl-containing ethylenically unsaturated monomer which provides hydroxyl functionality to the polymer; 1–20 percent by weight of an acid-containing ethylenically unsaturated monomer which provides carboxy functionality to the polymer; 1–20 percent by weight of an amine-containing ethylenically unsaturated monomer which provides amine functionality to the polymer; and 0 to 30 percent by weight of an ethylenically unsaturated monomer devoid of acid, amine and hydroxyl content; and
    b) a propellant in an amount sufficient to apply said solution to hair.

15. A hair fixative formulation as defined in claim 14 wherein said propellant is carbon dioxide.

16. A hair fixative formulation comprising:
    a) a solution of a hair fixative amphoteric polymer composition comprising 40–90 percent by weight of a hydroxyl-containing ethylenically unsaturated monomer which provides hydroxyl functionality to the polymer; 1–20 percent by weight of an acid-containing ethylenically unsaturated monomer which provides carboxy functionality to the polymer; 1–20 percent by weight of an amine-containing ethylenically unsaturated monomer which provides amine functionality to the polymer; and 0 to 40 percent by weight of an ethylenically unsaturated monomer devoid of acid, amine and hydroxyl content; and
    b) carbon dioxide propellant in an amount sufficient to apply said solution to hair and whereby the carbon dioxide is a neutralizing agent for the said polymer composition that is insoluble in water but solubilizable in water by the addition of a neutralizing agent.

17. A hair fixative amphoteric polymer composition comprising: 40–90 percent by weight of a hydroxyl-containing ethylenically unsaturated monomer which provides hydroxyl functionality to the polymer selected from the group consisting of: hydroxy alkyl acrylates and hydroxy alkyl methacrylates; 1–20 percent by weight of an acid-containing ethylenically unsaturated monomer which provides carboxy functionality to the polymer; 1–20 percent by weight of an amine-containing ethylenically unsaturated monomer which provides amine functionality to the polymer selected from the group consisting of: amine functional acrylates and methacrylates; and 0 to 29 percent by weight of an ethylenically unsaturated monomer devoid of acid, amine and hydroxyl content selected from the group consisting of: alkyl esters of acrylic and methacrylic and vinyl aromatic monomers, nitrile monomers, vinylesters, and vinylamides; said polymer composition being insoluble in water but solubilizable in water by at least one of the following solubilization steps;

1) addition of a neutralizing agent comprising an acid,
2) addition of a neutralizing agent comprising an amine, and
3) addition of a water miscible alcohol.

18. A hair fixative amphoteric polymer composition of claim 17,
    wherein the hydroxyl-containing ethylenically unsaturated monomer is selected from the group consisting of: hydroxyethyl acrylate, hydroxyethyl methacrylate, hydroxypropyl acrylate, hydroxypropyl methacrylate, hydroxybutyl acrylate, and hydroxybutyl methacrylate; and
    wherein the amine-containing ethylenically unsaturated monomer is selected from the group consisting of: N,N-dimethylaminoethyl methacrylate, tert-butylaminoethyl methacrylate, and N,N-diethylaminoethyl methacrylate; and
    wherein the ethylenically unsaturated monomer devoid of acid, amine and hydroxyl content is selected from the group consisting of: methyl methacrylate, ethyl methacrylate, butyl methacrylate, ethyl acrylate, butyl acrylate, 2-ethylhexyl acrylate, styrene, vinyl toluene, acrylonitrile, methacrylonitrile, vinyl acetate, acrylamide, N-alkylacrylamides and cyclic amides; and
    wherein the neutralizing agent, when an acid is selected, is from the group consisting of: carbonic, formic, acetic, lactic, and trifluoroacetic acid, and, when an amine is selected, is from the group consisting of: 2-dimethylaminoethanol, (N,N-dimethylethanolamine), 2-amino-2-methyl-1-propanol, 3-dimethylamino-1-propanol, 3-dimethylamino-2-propanol, 1-amino-2-propanol, ethanolamine, ammonia, and, when a water miscible alcohol is selected, is from the group consisting of: monohydric alcohol having 2 to 3 carbon atoms.

19. The hair fixative amphoteric polymer composition as defined in claim 1 wherein said ethylenically unsaturated monomer devoid of acid, amine and hydroxyl content is present in an amount of 10 to 20 percent by weight of the monomers for the polymer composition.

20. A hair fixative amphoteric polymer composition comprising:
    50–75 percent by weight of a hydroxyl-containing ethylenically unsaturated monomer which provides hydroxyl functionality to the polymer, wherein the hydroxyl-containing ethylenically unsaturated monomer is selected from the group consisting of: hydroxyethyl acrylate, hydroxyethyl methacrylate, hydroxypropyl acrylate, hydroxypropyl methacrylate, hydroxybutyl acrylate, and hydroxybutyl methacrylate;
    2–10 percent by weight of an acid-containing ethylenically unsaturated monomer which provides carboxy functionality to the polymer selected from the group consisting of acid-containing ethylenically unsaturated monomer is selected from the group consisting of acrylic acid, methacrylic acid, 10-undecenoic acid, crotonic acid, and beta-carboxyethyl acrylate;
    5–15 percent by weight of an amine-containing ethylenically unsaturated monomer which provides amine functionality to the polymer, wherein the amine-containing ethylenically unsaturated monomer is selected from the group consisting of: N,N-dimethylaminoethyl methacrylate, tert-butylaminoethyl methacrylate, and N,N-diethylaminoethyl methacrylate; and 10 to 20 percent by weight of an ethylenically unsaturated monomer devoid of acid, amine and hydroxyl content selected from the group consisting of styrene and methyl methacrylate; said polymer composition being insoluble in water but solubilizable in water by the addition of a compound selected from the group consisting of: A) acid neutralizing agent selected from the group consisting of carbonic, formic, acetic, lactic, and trifluoroacetic acid; B) amine neutralizing agent selected from the group consisting of: N,N-dimethylethanolamine, 2-amino-2-methyl-1-propanol, 3-dimethylamino-1-propanol, 3-dimethylamino-2-propanol, 1-amino-2-propanol, ethanolamine, and ammonia; and (C) water miscible alcohol, and said polymer having a number average molecular weight of between 1,500 and 100,000 and a glass transition temperature of between 40–80° C.

21. A hair fixative amphoteric polymer composition comprising: 40–90 percent by weight of a hydroxyl-containing ethylenically unsaturated monomer which provides hydroxyl functionality to the polymer; 1–10 percent by weight of an acid-containing ethylenically unsaturated monomer which provides carboxy functionality to the polymer; 1–20 percent by weight of an amine-containing ethylenically unsaturated monomer which provides amine functionality to the polymer; and 0 to 30 percent by weight of an ethylenically unsaturated monomer devoid of acid, amine and hydroxyl content; and wherein the total of the weight percentages for the monomers is 100 and said polymer composition being insoluble in water but solubilizable in water by at least one of the following solubilization steps;

1) addition of a neutralizing agent comprising an acid, 2) addition of a water miscible alcohol.

* * * * *

UNITED STATES PATENT AND TRADEMARK OFFICE
CERTIFICATE OF CORRECTION

PATENT NO.  : 5,948,396
DATED       : September 7, 1999
INVENTOR(S) : Suryya K. Das, Soner Kilic, William C. Allison It is certified that error appears in the above-identified patent and that said Letters Patent is hereby corrected as shown below:

Claim 6, line 4   Delete [dimethylethanolamines] and insert --dimethylethanolamine;--.
Claim 12, line 5  Delete [1-20] and insert --1-10--.
Claim 12, line 10 Delete [0 to 40] and insert --0 to 30--.
Claim 13, line 10 Delete [0 to 40] and insert --0 to 30--.

Signed and Sealed this

First Day of August, 2000

Attest:

Q. TODD DICKINSON

Attesting Officer          Director of Patents and Trademarks